(12) United States Patent
Fini

(10) Patent No.: US 9,067,025 B2
(45) Date of Patent: Jun. 30, 2015

(54) SAFETY INSERT FOR EXTRA-CORPOREAL CIRCUITS

(75) Inventor: Massimo Fini, Mirandola (IT)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 292 days.

(21) Appl. No.: 13/321,023

(22) PCT Filed: May 14, 2010

(86) PCT No.: PCT/EP2010/056640
§ 371 (c)(1),
(2), (4) Date: Jan. 19, 2012

(87) PCT Pub. No.: WO2010/133515
PCT Pub. Date: Nov. 25, 2010

(65) Prior Publication Data
US 2012/0114886 A1 May 10, 2012

(30) Foreign Application Priority Data
May 19, 2009 (EP) ..................................... 09160691

(51) Int. Cl.
*B01D 35/14* (2006.01)
*A61M 1/36* (2006.01)
*G01L 19/00* (2006.01)
*G01L 19/06* (2006.01)

(52) U.S. Cl.
CPC ............. *A61M 1/3639* (2013.01); *Y10T 428/13* (2015.01); *A61M 2205/15* (2013.01); *A61M 2205/16* (2013.01); *A61M 2205/7536* (2013.01); *G01L 19/003* (2013.01); *G01L 19/0636* (2013.01); *A61M 1/3641* (2014.02)

(58) Field of Classification Search
CPC ..................... A61M 2205/15; A61M 2205/16; A61M 2001/3641; A61M 1/3639; A61M 1/3653; A61M 1/3621; A61M 1/2663; G01L 19/06
USPC .......... 428/34.1, 35.7; 210/232, 321.6, 327.15
See application file for complete search history.

(56) References Cited

U.S. PATENT DOCUMENTS 8,287,730 B2 * 10/2012 Reiter et al. ................... 210/232

FOREIGN PATENT DOCUMENTS

| EP | 1 547 630 | 6/2005 |
| EP | 1 605 990 | 12/2005 |
| EP | 1 728 526 | 12/2006 |
| WO | WO 2004/082732 | 9/2004 |

* cited by examiner

*Primary Examiner* — Yan Lan
(74) *Attorney, Agent, or Firm* — Jacobson Holman, PLLC.

(57) ABSTRACT

A safety insert for an extra-corporeal circuit includes a first half-shell and a second half-shell forming a shell defining an inner duct, at least part of the second half-shell being made with a translucent material; a first connector to be connected to the extra-corporeal circuit, and a second connector to be connected to a transducer; and a first hydrophobic semi-permeable membrane having a first area $A_1$ and a second hydrophobic semi-permeable membrane having a second area $A_2$, with the two membranes being arranged in series along the inner duct. In a front view, the extent of an overlapping area $A_{12}$ of the membranes is between 0% and 50% of the smaller of the two areas $A_1$, $A_2$. An extra-corporeal circuit includes the safety insert.

13 Claims, 9 Drawing Sheets

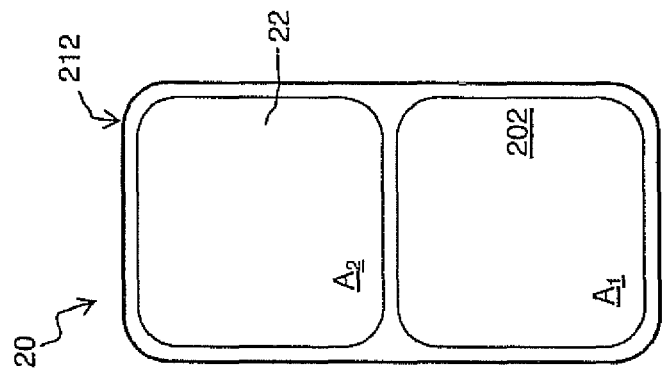
Fig. 9.a
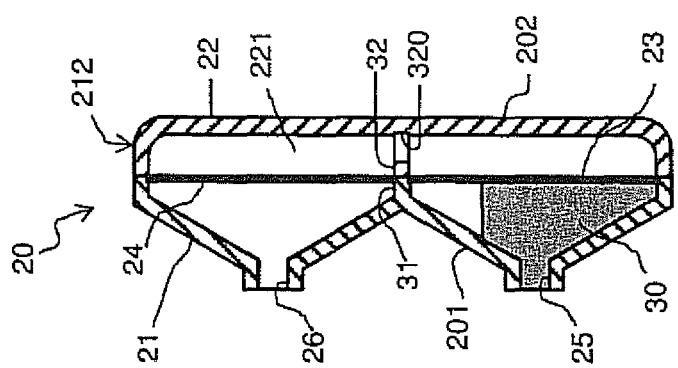
Fig. 9.b
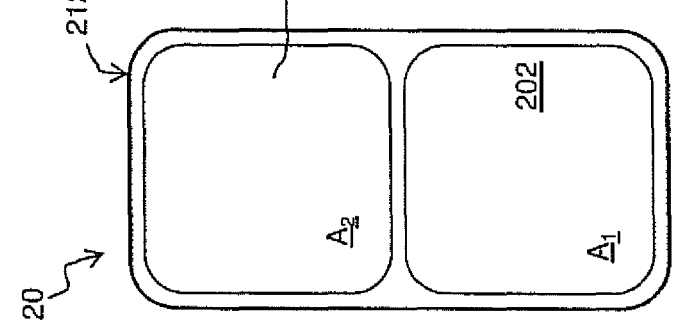
Fig. 10.a
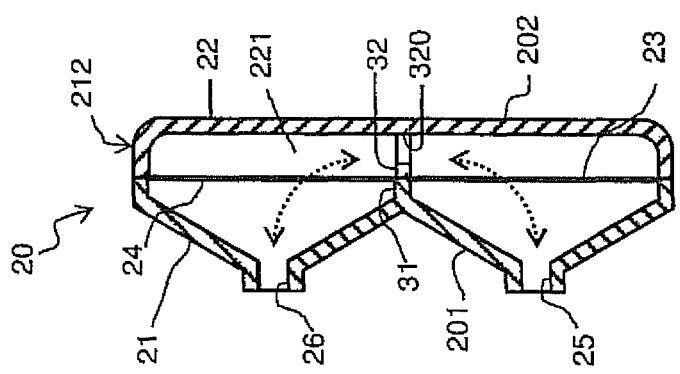
Fig. 10.b

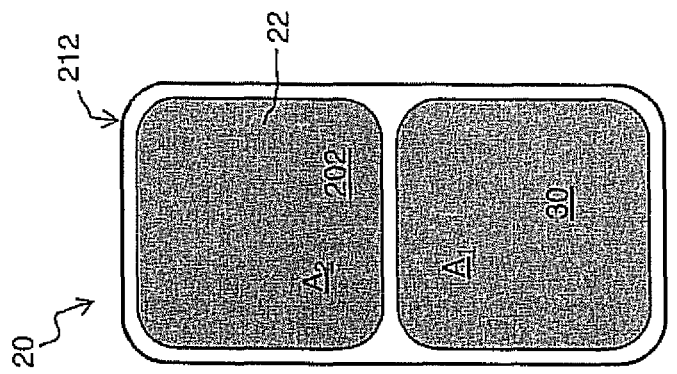
Fig. 12.b
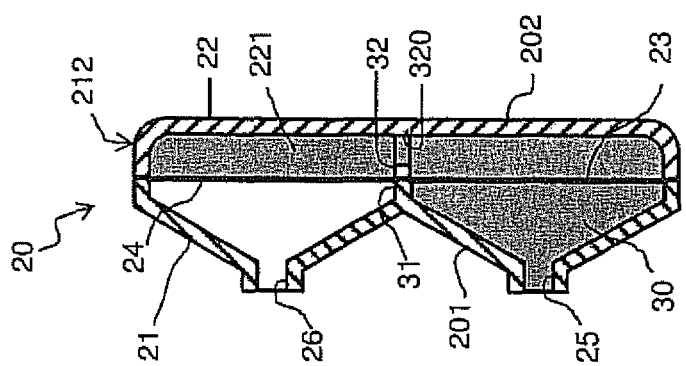
Fig. 12.a
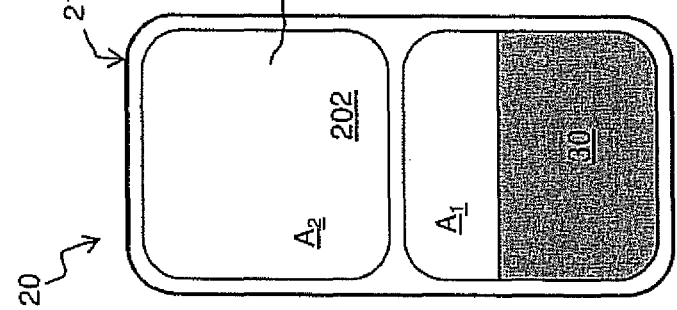
Fig. 11.b
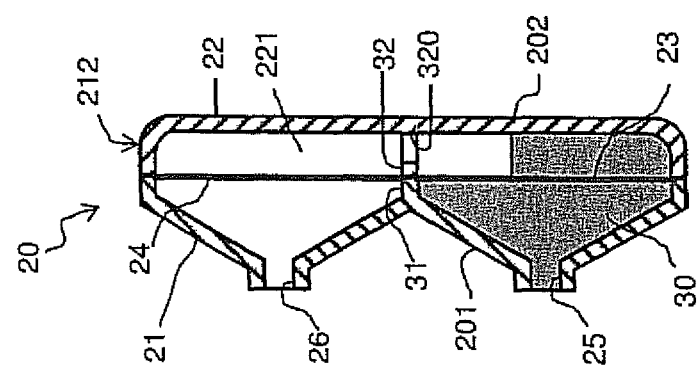
Fig. 11.a

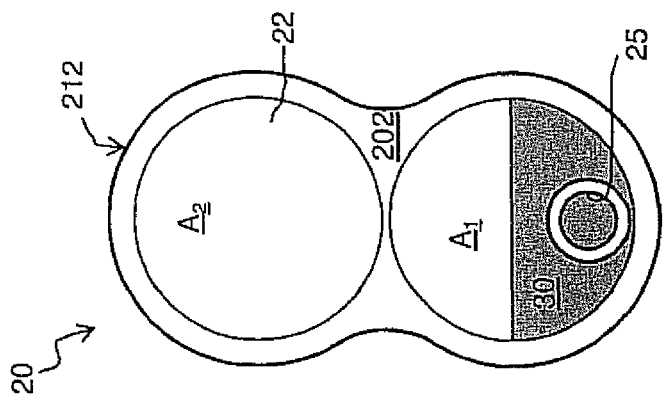
Fig. 15.b
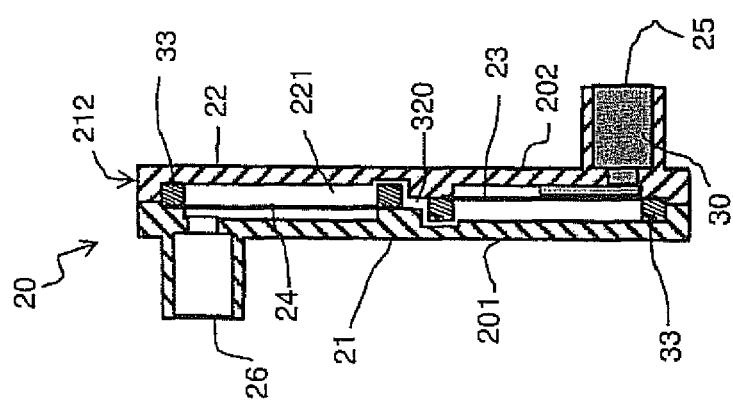
Fig. 15.a

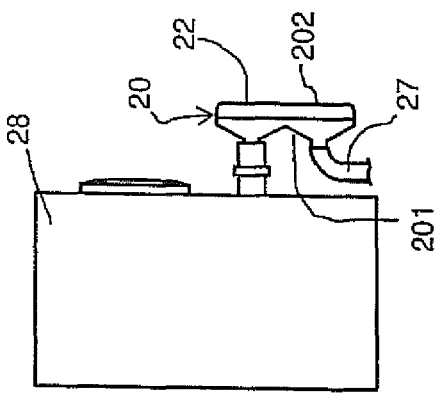
Fig. 18.b
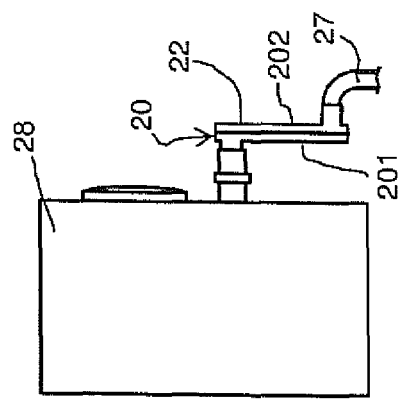
Fig. 19.b
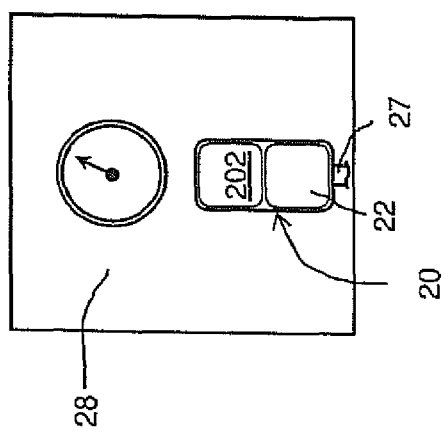
Fig. 18.a
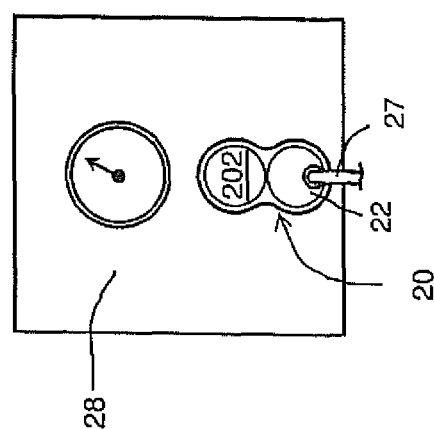
Fig. 19.a

SAFETY INSERT FOR EXTRA-CORPOREAL CIRCUITS

CROSS-REFERENCE TO RELATED APPLICATIONS

This is a national stage of PCT/EP10/056640 filed May 14, 2010 and published in English, which claims the priority of European number 09160691.3 filed May 19, 2009, hereby incorporated by reference.

BACKGROUND OF THE INVENTION

1. Field of Invention

The invention relates to a safety insert for extra-corporeal circuits, in particular a transducer protector for preventing contamination of a pressure gauge on the extra-corporeal circuit.

2. Description of the Prior Art

In therapeutic treatments which require an extra-corporeal circulation system, such as haemodialysis, the arterial and venous pressure in the extra-corporeal circuit must be constantly monitored. This is achieved in a manner known per se by means of pressure transducers connected to the main circuit via suitable branch pipes. In an equally known manner, a safety insert or transducer protector is positioned between the pipe and the pressure transducer in order to avoid any possible contact between the patient's blood and the machine (artificial kidney). In fact, the extra-corporeal circuit is made of disposable material, while the artificial kidney as a whole must, of necessity, be continuously reused.

The transducer protector is formed, in a manner known per se, by means of a plastic shell enclosing a hydrophobic gas permeable membrane. Each side of the shell comprises a tubular connector. A first tubular connector is designed to be connected to the branch pipe, while the other tubular connector is designed to be connected to the pressure transducer.

Due to pressure fluctuations, the patient's blood can enter the branch pipe and the first tubular connector. In such a case, the membrane is intended to stop the blood flow so as to prevent contamination of the machine. In a minor number of cases, the membrane can leak or even break and a contamination of the machine can occur without any notice of the service personnel.

In order to increase the overall safety margin of the system, also such a rare incident should be avoided. Double transducer protectors have been provided for this reason.

According to its first version, the double transducer protector simply comprises two membranes in series. Such device is very simple, but its effectiveness in reducing the risk of contamination relies on a merely statistical basis. A transducer protector of this type is disclosed in EP 1 605 990.

Other versions of double transducer protectors have two membranes in series and means to detect the presence of a contaminant between the membranes. Such devices are adapted to alert the service personnel in case of leakage of the first membrane, thus actually increasing the overall safety margin. In turn, such devices are quite complex and require additional components for the system. Transducer protectors of this type are disclosed in EP 1 547 630 and in EP 1 728 526.

SUMMARY OF THE INVENTION

The object of the present invention is therefore to solve at least partially the drawbacks identified in connection with the transducer protectors of the known types.

An aim of the present invention is to provide a transducer protector for extra-corporeal circuits which provides a greater intrinsic safety margin.

In particular, an aim of the present invention is to provide a transducer protector with a very simple and inexpensive structure.

Furthermore, an aim of the present invention is to provide a transducer protector which permits to the service personnel to opportunely detect a failure and to intervene at the right time.

The abovementioned object and aims are achieved by a transducer protector as described herein.

BRIEF DESCRIPTION OF THE DRAWINGS

The characteristic features and further advantages of the invention will emerge more clearly from the following description provided below, of a number of examples of embodiment, described by way of a non-limiting example, with reference to the accompanying drawings in which;

FIG. 9.a shows a side cross-section view of the transducer protector of FIG. 4, in a first operating configuration;

FIG. 9.b shows a front view of the transducer protector of FIG. 9.a;

FIG. 10.a shows a side cross-section view of the transducer protector of FIG. 4, in a second operating configuration;

FIG. 10.b shows a front view of the transducer protector of FIG. 10.a;

FIG. 11.a shows a side cross-section view of the transducer protector of FIG. 4, in a third operating configuration;

FIG. 11.b shows a front view of the transducer protector of FIG. 11.a;

FIG. 12.a shows a side cross-section view of the transducer protector of FIG. 4, in a fourth operating configuration;

FIG. 12.b shows a front view of the transducer protector of FIG. 12.a;

FIG. 15.a shows a side cross-section view of the transducer protector of FIG. 13, in an operating configuration similar to that of FIG. 10.a;

FIG. 15.b shows a front view of the transducer protector of FIG. 15.a;

FIG. 18.a is a front view of a detail similar to that of FIG. 2, in an extra-corporeal circuit comprising the transducer protector of FIG. 4;

FIG. 18.*b* is a side view of the detail of FIG. 18.*a*;

FIG. 19.*a* is a front view of a detail similar to that of FIG. 2, in an extra-corporeal circuit comprising the transducer protector of FIG. 14;

FIG. 19.*b* is a side view of the detail of FIG. 19.*a*.

DETAILED DESCRIPTION OF THE PREFERRED EMBODIMENTS

Figure 2:
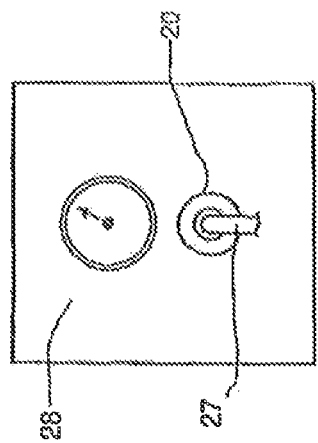
FIG. 2 is a front view of the detail indicated with II in the extra-corporeal circuit of FIG. 1.
Figure 3:
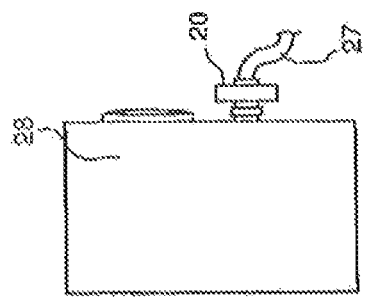
FIG. 3 is a side view of the detail of FIG. 2.
Figure 1:
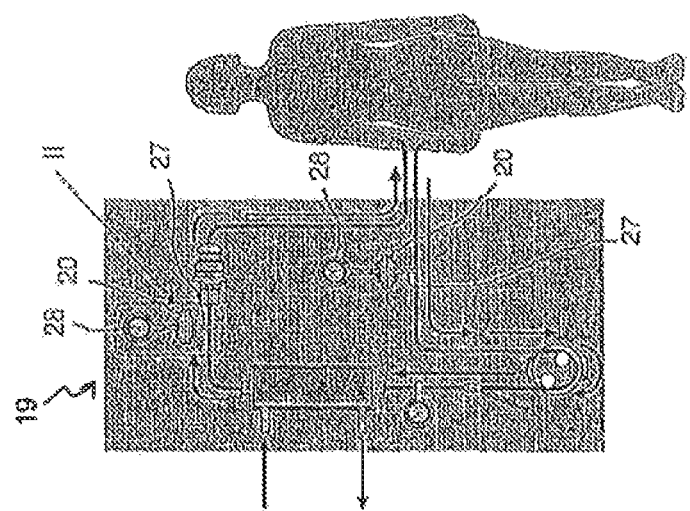
FIG. 1 shows in schematic form an extra-corporeal circuit used in therapeutic treatment according to the prior art.
Figure 6:
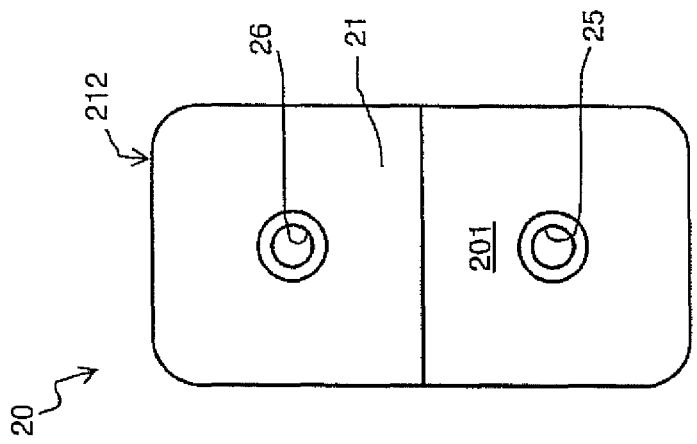
FIG. 6 shows a rear view of the transducer protector of FIG. 4.
Figure 5:
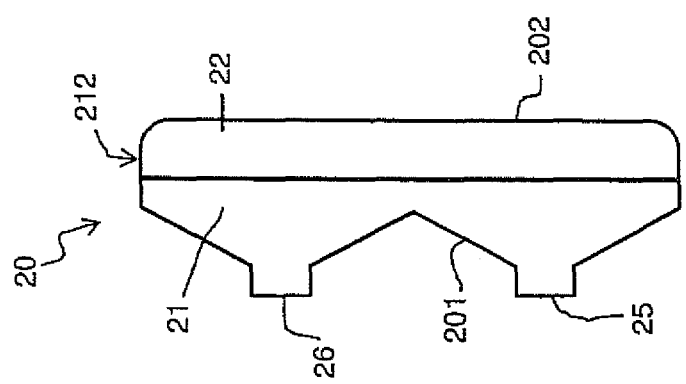
FIG. 5 shows a side view of the transducer protector of FIG. 4.
Figure 4:
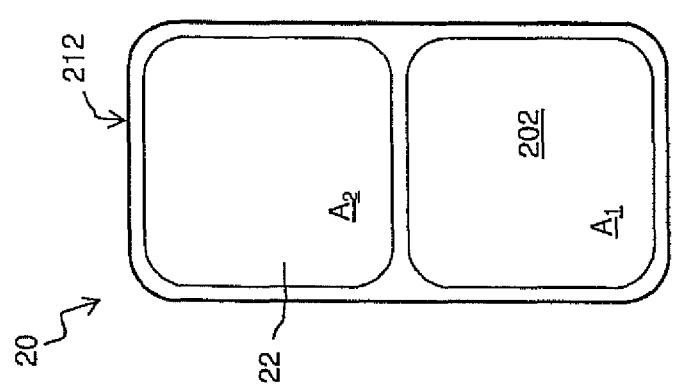
FIG. 4 shows a front view of a transducer protector according to the invention.
Figure 7:
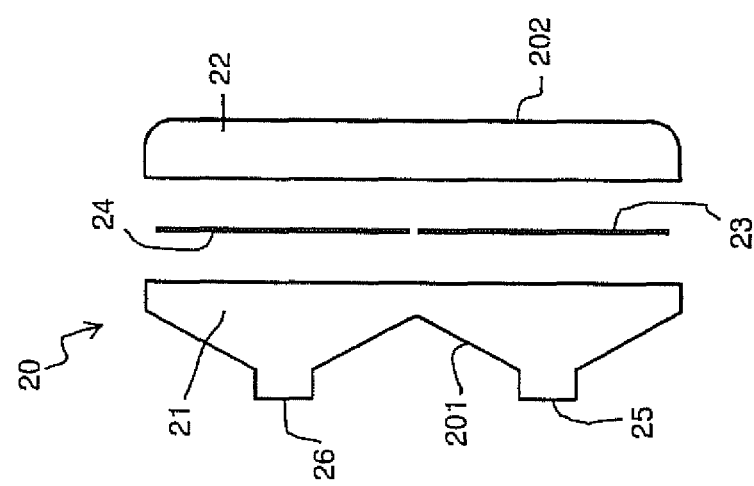
FIG. 7 shows a side exploded view of the transducer protector of FIG. 4.
Figure 8:
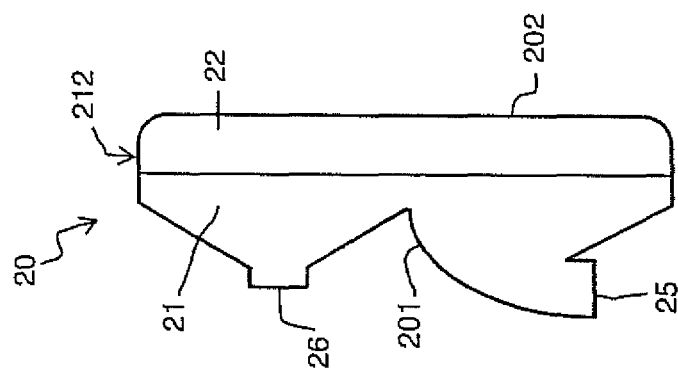
FIG. 8 shows a side view of another transducer protector according to the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention relates to a safety insert 20 for an extra-corporeal circuit 19. The safety insert 20, or transducer protector, comprises:

a first half-shell 21 and a second half-shell 22 forming a shell 212 defining an inner duct 221, at least part of the second half-shell 22 being made with a translucent or transparent material;

a first tubular connector 25 adapted to be connected to a branch pipe 27 from the extra-corporeal circuit 19, and a second tubular connector 26 defined by the first half-shell 21 and adapted to be connected to a transducer 28; and a first hydrophobic semi-permeable membrane 23 having a first membrane area $A_1$ and a second hydrophobic semi-permeable membrane 24 having a second membrane area $A_2$, said two membranes 23, 24 being arranged in series along said inner duct 221.

In the safety insert 20 according to the invention, in a front view, the extent of an overlapping area $A_{12}$ of said membranes 23, 24 is comprised between 0% and 50% of the smaller of said two membrane areas $A_1$, $A_2$.

In the enclosed FIGS. 18 and 19, the transducer protector 20 is shown properly arranged in its operation configuration, i.e. connected both to the branch pipe 27 and to the transducer 28. With reference also to such figures, the operation configuration of the transducer protector 20 defines a back 201 and a front 202. Here and below, the terms "back", "backward", "rear" and the like, refer to positions in the transducer protector 20 relatively close, in use, to the panel of the transducer 28. On the other hand, the terms "front", "forward", "ahead" and the like, refer to positions relatively distant from the panel of the transducer 28.

According to the invention, at least part of the second half-shell 22 is made with a translucent or transparent material, e.g. polycarbonate or other medical grade materials. According to different embodiments of the invention, the translucent portion may be provided at different extents. For example, the whole second half-shell 22 may be made with a translucent or transparent material. Preferably, the whole shell 212 is translucent, i.e. both the first half-shell 21 and the second half-shell 22 are made with a translucent material.

As already pointed out, in a front view, the extent of the overlapping area $A_{12}$ of said membranes 23, 24 is very small. In particular, the overlapping area $A_{12}$ is comprised between 0% and 50% of the smaller of the two membrane areas $A_1$, $A_2$.

A possible definition of "overlapping" is given below, even if many other definitions are possible. The membranes 23 and 24 overlap in a front view if a straight line perpendicularly passing through the first membrane 23 passes also through the second membrane 24, or vice versa. Of course such definition directly implies a definition of the overlapping area $A_{12}$. However, notwithstanding the definition, the skilled person will easily understand the meaning of such wording, especially in view of the following.

Figure 17:
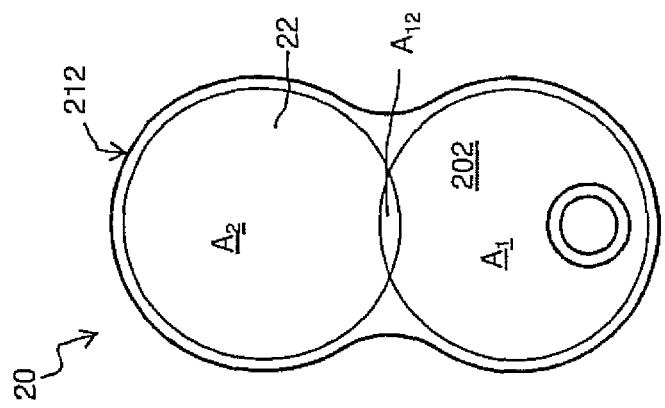
FIG. 17 shows a front view of a transducer protector according to the invention.
Figure 16:
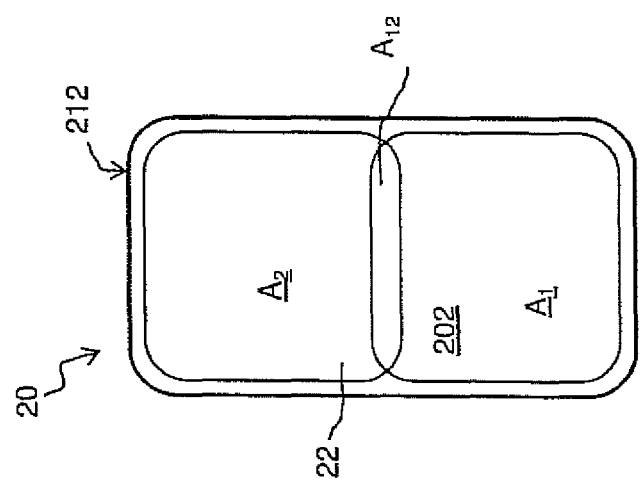
FIG. 16 shows a front view of a transducer protector according to the invention.

According to many embodiments, the extent of the overlapping area $A_{12}$ is equal to 0, i.e. the membranes 23 and 24 do not overlap at all. FIGS. 4 to 15, 18 and 19 show such kind of embodiments. On the contrary, FIGS. 16 and 17 show front views of two different embodiments of the invention wherein the extent of the overlapping area $A_{12}$ is greater than zero, i.e. the membranes 23 and 24 do overlap.

According to many embodiments of the invention, each of said first and second membrane 23 and 24 is arranged in a planar configuration. In particular, the two membranes 23 and 24 can advantageously lie on parallel planes. Moreover, the two membranes 23 and 24 can advantageously lie on the same plane.

According to an embodiment of the invention, the colour of the membranes 23 and 24 is very light, preferably white.

According to some embodiments of the invention (see for example FIGS. 4 to 12, 16 and 18), both the first and the second tubular connectors 25 and 26 are defined by the first half-shell 21. In other words, both the tubular connectors 25 and 26 are placed on the back 201 of the transducer protector 20. Accordingly, in such embodiments, the front 202 of the transducer protector 20 is completely plain. In other words, the front 202 is free from any element which could prevent or even reduce its visibility.

According to such embodiments (see for example FIG. 9.*a*), the duct 221 starts on the back 201 at the first tubular connector 25, it goes forward through the first membrane 23, then it goes back through the second membrane 24 and it ends again on the back 201, at the second tubular connector 26.

According to the embodiments of FIGS. 4 to 12, 16 and 18, said first membrane 23 and said second membrane 24 can be obtained either by means of two separate pieces of a suitable film, or by means of a single piece. In any case, the two membranes have to be firmly separated one from the other on their back. In this manner, the duct 221 goes forward through the first membrane 23 and then goes back through the second membrane 24 rather than passing on the back of the two membranes. According to the embodiment shown in the attached figures, such firm separation is obtained by means of two ribs 31 and 32 of the first half-shell 21 and the second half-shell 22 respectively. The second rib 32 of the second half-shell 22 defines a passageway 320 intended to guarantee the continuity of the duct 221.

According to some other embodiments of the invention (see for example FIGS. 13-15, 17 and 19), while the second tubular connector 26 is defined by the first half-shell 21, the first tubular connector 25 is defined by the second half-shell 22. In other words, the second tubular connector 26 is placed on the back 201 of the transducer protector 20, while the first tubular connector 25 is placed on its front 202.

According to such embodiments (see FIG. 15.*a*), the duct 221 starts on the front 202 at the first tubular connector 25, it goes backward through the first membrane 23, then it goes forward along the passageway 320, it goes backward again through the second membrane 24 and it ends on the back 201, at the second tubular connector 26.

According to the embodiments of FIGS. 13-15, 17 and 19, said first membrane 23 and said second membrane 24 are preferably obtained by means of two separate pieces, in order to let the passageway 320 pass between them, but they can be one single piece since the passageway 320 can be lateral. According to the embodiment shown in the attached figures, the membranes 23 and 24 are firmly held in place by means of two rings 33, otherwise they can be directly welded to the body of the half shells 21 and 22. The half-shells 21 and 22 define, in their mid zone, the passageway 320 intended to guarantee the continuity of the duct 221.

FIGS. 9 to 12 show different operating configurations of a transducer protector 20 according to the embodiment of FIGS. 4-7 and 18. FIG. 9.*a* shows a cross-section view of the transducer protector during its normal operation. In such conditions the inner duct 221 contains air only, in order to provide the pressure of the branch pipe 27 to the transducer 28. Air can flow along the inner duct 221: it enters the tubular connector 25, passes through the first membrane 23, through the passageway 320, through the second membrane 24 and exits the tubular connector 26. Of course, according to the pressure variation, air can also flow backwards along the inner duct 221. These flows are schematically indicated by means of the double dotted arrows in FIG. 9.*a*. FIG. 9.*b* shows a front view of the same transducer protector during its normal operation, i.e. FIG. 9.*b* shows what the service personnel can see while looking at the transducer protector. As can be appreciated, the transducer protector, during its normal operation, is completely clear.

FIG. 10.*a* shows a cross-section view of the transducer protector 20 after the patient's blood 30, due to pressure fluctuations, has entered the branch pipe 27 and the first tubular connector 25. The first membrane 23 has duly stopped the blood flow so as to prevent contamination of the pressure transducer 28. In FIG. 10.*a*, the portion of the inner duct 221 comprised between the first tubular connector 25 and the first membrane 23 has evidently a different colour with respect to the same portion of FIG. 9.*a*. It should be noted here that the light grey colour of the attached black-and-white FIGS. 10.*a*, 11-12 and 15 would be actually bright red in facts. Also the front view of the transducer protector 20, in such conditions, would probably show a slight change in the colour of the first membrane 23. However such slight change is not considered to be sufficiently evident in order to be a reliable warning signal for the service personnel. Accordingly, FIG. 10.*b* shows a completely clear transducer protector 20 like FIG. 9.*b*.

In a minor number of cases, the first membrane 23 can leak or even break so as to let the blood flow through it. FIG. 11.*a* shows a cross-section view of the transducer protector 20 after the patient's blood 30 has passed through the first membrane 23. In FIG. 11.*a*, the portion of the inner duct 221 comprised between the first membrane 23 and the second membrane 24 has partially changed colour with respect to the previous FIGS. 9.*a* and 10.*a*. In such conditions, also the front view of the transducer protector 20 (FIG. 11.*b*) shows an evident change in its colour, turning to a bright red in facts (light grey in the figures). Such change is sufficiently evident to be an actual warning signal for the service personnel.

FIG. 12.*a* shows a cross-section view of the transducer protector 20 after the patient's blood 30 has completely filled the whole portion of the inner duct 221 comprised between the first membrane 23 and the second membrane 24. The second membrane 24 has duly stopped the blood flow so as to prevent contamination of the transducer. In such conditions, the front view of the transducer protector 20 (FIG. 12.*b*) shows an evident and total change in its colour, turning to a bright red in facts (light grey in the figures). Such change, due to the sharp contrast between the very light colour of the membranes and the bright red of blood, is very evident for the service personnel.

Figure 14:
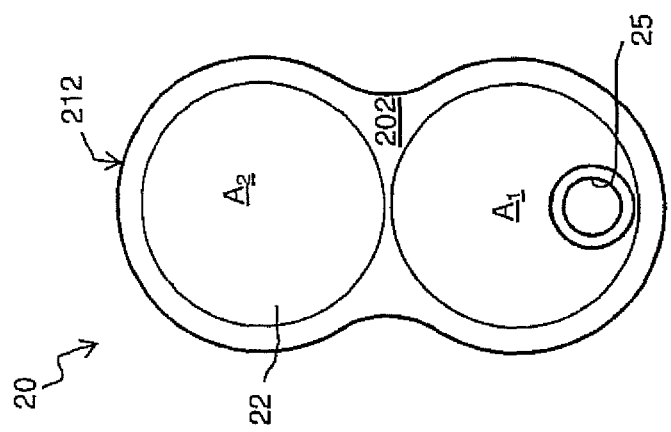
FIG. 14 shows a front view of the transducer protector of FIG. 13.
Figure 13:
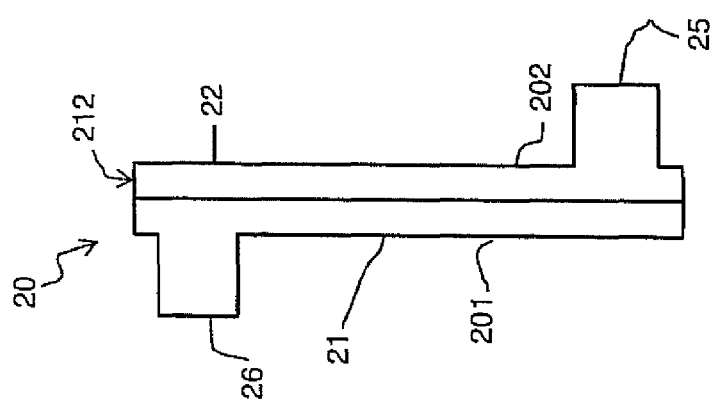
FIG. 13 shows a side view of a further transducer protector according to the invention.

FIG. 15 show different operating configurations of a transducer protector 20 according to the embodiment of FIGS. 13 and 14. FIG. 15.*a* shows a cross-section view of the transducer protector, similar to the one of FIG. 10.*a*. In particular, FIG. 15.*a* shows a cross-section view of the transducer protector 20 after the patient's blood 30, due to pressure fluctuations, has entered the branch pipe 27 and the first tubular connector 25. The first membrane 23 has duly stopped the blood flow so as to prevent contamination of the pressure transducer 28. In a different manner with respect to the same condition described with respect to FIG. 10, in FIG. 15 also the front view of the transducer protector 20 (FIG. 15.*b*), shows an evident change in the colour of the first membrane 23. Such change is sufficiently evident to be an actual warning signal for the service personnel. In other words, according to the embodiment of FIGS. 13-15, a warning signal is available for the service personnel immediately after the patient's blood 30 has entered the first tubular connector 25. As can be easily appreciated by the skilled person, the earlier the warning signal, the larger the safety margin to avoid any problem.

Of course, as already pointed out with respect to the prior art double transducer protectors, the presence of two membranes in series is effective in reducing the risk of contamination on a merely statistical basis. However, it should be noted that the specific arrangement of the transducer protectors 20 according to the invention, not only provides two membranes in series, but also permits the service personnel to opportunely detect a failure and to intervene at the right time. In fact, the blood 30 takes a lot of time to completely fill the portion of the inner duct 221 comprised between the first membrane 23 and the second membrane 24 so as to reach the configuration of FIG. 12. During such period of time the service personnel can easily detect the failure and intervene in order to solve the problem. It should be noted here that, with reference to FIG. 11, the transducer protector 20 has a preferable (or "right") vertical orientation for its connection to the circuit 19. As can be appreciated in FIGS. 11 and 15, the patient's blood 30 gathers, due to gravity, in a specific portion of the duct 221. It is thus possible to define a lower portion (collecting blood 30) and an opposite upper portion.

In view of the above, in the right orientation of the transducer protector 20, the first tubular connector 25 is placed under the second tubular connector 26. According to an opposite (or "wrong") orientation of the transducer protector 20, wherein the first tubular connector 25 is placed over the second tubular connector 26, the blood 30 would take a shorter period of time to completely fill the portion of the duct 221 comprised between the two membranes 23 and 24. Accordingly, the wrong orientation of the transducer protector 20 provides a reduced safety margin for detecting and solving a problem.

In some embodiments of the invention, the first tubular connector 25 is specifically designed to be connected to the branch pipe 27, while the second tubular connector 26 is specifically designed to be connected to the transducer 28. According to such embodiments, due to the differences between the first and the second tubular connectors, the right orientation can be defined for the transducer protector 20 taken alone.

On the contrary, according to some other embodiments of the invention, the first and second tubular connectors are indistinguishable one from the other. According to such embodiments, the right orientation can be defined for the transducer protector 20 only with respect to the circuit 19 and the connections thereto.

As the skilled person may easily appreciate, the transducer protector 20 according to the invention permits to overcome almost completely the drawbacks pointed out with respect to the prior art. In fact, the front 202 of the transducer protector 20 is intended to be widely visible all along the operation. In particular, if the patient's blood 30 passes the first membrane 23 due to a leakage and enters the second half-shell 22, the translucent portion of the latter openly changes colour, typically from white to bright red. The possibility to easily see the second half-shell 22, because of the tubular connectors being on the back, and its change of colour, because of the presence of blood 30 therein, enable the service personnel to opportunely detect the failure and to intervene at the right time.

It should be noted here that during normal operation of the transducer protector 20, service personnel can reasonably see the transducer protector 20 only from a front or, at most, a side point of view, see FIGS. 18 and 19. In fact the transducer protector 20 is connected on its back to the panel of the transducer 28 which completely prevents the rear view. As a consequence, according to the invention, a leakage of the first membrane implies an evident change in the colour of the front 202 of the transducer protector 20.

Moreover, since front visibility is much more relevant than back visibility, according to some embodiments, the front 202 is completely free from hindrance for the service personnel's sight.

With regard to the embodiments of the transducer protector described above, the person skilled in the art may, in order to satisfy specific requirements, make modifications to and/or replace elements described with equivalent elements, without thereby departing from the scope of the accompanying claims.

What is claimed is:

1. A safety insert or transducer protector for an extra-corporeal circuit, comprising:
    a first half-shell and a second half-shell forming a shell defining an inner duct, at least part of the second half-shell having a material of construction that is translucent or transparent;
    a first tubular connector adapted to be connected to a branch pipe from the extra-corporeal circuit, and a second tubular connector defined by the first half-shell and adapted to be connected to a transducer; and
    a first hydrophobic semi-permeable membrane having a first membrane area ($A_1$) and a second hydrophobic semi-permeable membrane having a second membrane area ($A_2$), said first and second membranes (i) being arranged in series along said inner duct and (ii) lying in substantially a same plane,
    with an overlapping area ($A_{12}$) of said first and second membranes being between 0% and 50% of a lesser of the first and second membrane areas ($A_1$, $A_2$).

2. The insert according to claim 1, wherein an entirety of the second half-shell has the material of construction that is translucent or transparent.

3. The insert according to claim 1, wherein the first half-shell and the second half-shell have a material of construction that is translucent.

4. The insert according to claim 1, wherein the first and second membranes are light colored.

5. The insert according to claim 4, wherein the first and second membranes are white.

6. The insert according to claim 1, wherein the safety insert is configured for viewing from a perspective that is substantially perpendicular to the plane of the first and second membranes.

7. The insert according to claim 1, wherein an operation configuration thereof defines a back of the insert, facing the transducer, and a front of the insert.

8. The insert according to claim 1, wherein the first tubular connector is defined by the first half-shell.

9. The insert according to claim 8, wherein a front of the insert is completely plain and free from any element which could prevent or reduce the visibility thereof.

10. The insert according to claim 1, wherein the first tubular connector is defined by the second half-shell.

11. The insert according to claim 1, wherein said first and second membranes lie on a same plane.

12. An extra-corporeal circuit comprising at least one safety insert according to claim 1.

13. The extra-corporeal circuit according to claim 12, wherein the first tubular connector connected to the branch pipe is placed under the second tubular connector connected to the transducer.

* * * * *